US00PP11202P

United States Patent [19]

Smith et al.

[11] Patent Number: Plant 11,202

[45] Date of Patent: Feb. 1, 2000

[54] PANICUM PLANT NAMED 'DALLAS BLUES'

[76] Inventors: Linda L. Smith; Kenneth E. Smith, both of 2262 Hard Rd., Columbus, Ohio 43235

[21] Appl. No.: 09/092,408

[22] Filed: Jun. 8, 1998

[51] Int. Cl.[7] ..... A01H 5/00

[52] U.S. Cl. ..... Plt./384

[58] Field of Search ..... Plt./388, 395, 384

*Primary Examiner*—Howard J. Locker
*Assistant Examiner*—Wendy Anne Baker
*Attorney, Agent, or Firm*—C. A. Whealy

[57] ABSTRACT

A new and distinct cultivar of Panicum plant named 'Dallas Blues', characterized by its large grayed blue-green leaves; large, dense plant habit; moderate to vigorous growth rate; late flowering; rich winter foliage color; and very large panicles that are maintained throughout the winter and into the spring providing ornamental interest.

3 Drawing Sheets

BACKGROUND OF THE INVENTION

The present invention relates to a new and distinct cultivar of *Panicum virgatum* plant, hereinafter referred to by the cultivar name Dallas Blues.

The new Panicum was discovered and selected by the Inventors as a naturally-occurring seedling in a group of open-pollinated seedlings from a crossing of unidentified selections of *Panicum virgatum* in a garden in Dallas, Tex.

Asexual reproduction of the new Panicum by divisions taken over time since 1994, in Columbus, Ohio, has shown that the unique features of this new Panicum are stable and reproduce true to type in successive propagations.

SUMMARY OF THE INVENTION

The new Panicum has not been observed under all possible environmental conditions. The phenotype may vary somewhat with variations in environment such as temperature, daylength, light intensity, soil types, and water/fertility levels without, however, any variance in genotype. The following observations, measurements, values, and comparisons describe plants of the new Panicum grown in Columbus, Ohio, under outdoor conditions which closely approximate those generally used in commercial horticulture and garden practice.

The following characteristics have been repeatedly observed and are determined to be basic characteristics of 'Dallas Blues', which in combination distinguish this Panicum from other varieties of Panicum, specifically the non-patented *Panicum virgatum* cultivar Cloud Nine, and distinguish 'Dallas Blues' as a new and distinct cultivar:

1. Plants of the new Panicum have unusually wide leaf blades that are grayed blue-green in color. Plants of the cultivar Cloud Nine and other similar Panicum cultivars have much narrower leaves and are not as blue in color.

2. Plants of the new Panicum begin flowering in early September which is usually much later than other Panicum cultivars.

3. Plants of the new Panicum have very large, rigidly structured panicles. The panicles and supporting culm have a distinct purple cast making the large flower structure more conspicuous. Panicles of plants of the cultivar Cloud Nine and other Panicums are smaller and lack the purple cast.

4. Plants of the new Panicum maintain the panicle rachis throughout the winter and into the spring. Plants of the cultivar Cloud Nine and other Panicum cultivars do not maintain the ornamentally desirable panicle rachis throughout the winter.

5. When plants of the cultivars Dallas Blues and Cloud Nine are grown side-by-side, plants of the new Panicum are more vigorous, faster growing and produce larger, denser plants than the cultivar Cloud Nine.

6. The winter foliage color of plants of the new Panicum is rust brown when plants are grown in fertile soil and warm tan when grown in less fertile soil. The winter foliage color of plants of the cultivar Cloud Nine and other Panicums is light tan regardless of soil fertility.

BRIEF DESCRIPTION OF THE PHOTOGRAPHS

The accompanying colored photographs illustrate the overall appearance of the new Panicum, showing the colors as true as it is reasonably possible to obtain in colored reproductions of this type.

The photograph on the first sheet comprises a side perspective view of typical plants of the new Panicum beginning to flower in early September in Columbus, Ohio, showing the plant habit.

The photograph on the second sheet comprises a close-up view of the foliage showing the color.

The photograph on the third sheet comprises a side perspective view of the rachis and seed in February in Columbus, Ohio, showing the winter color and the durability of the rachis. Foliage and flower colors may appear different in the photographs than the actual colors due to light reflectance.

DETAILED BOTANICAL DESCRIPTION

The following description of the new Panicum is based on plants produced in Columbus, Ohio, under full sun outdoor conditions with average day temperatures ranging from 16 to 34° C. and average night temperatures ranging from 7 to 21° C. Color references are made to The Royal Horticultural Society Colour Chart except where general terms of ordinary dictionary significance are used.

Botanical classification: *Panicum virgatum* cultivar Dallas Blues.

Parentage: Naturally-occurring seedling selection from an open-pollinated crossing of unidentified selections of *Panicum virgatum.*

Propagation:

*Type.*—By divisions.

*Root description.*—Vigorous, fibrous, wiry, tough, pale yellow to creamy white, about 2 mm in diameter.

Plant description:

*General appearance.*—Herbaceous perennial grass with upright vase shape and dense habit; very large panicles. Flowering late, but rachis is maintained for an unusually long period, typically throughout the winter and into the spring. Moderate to vigorous growth rate. Appropriate for containers up to a 3-gallon size. To produce a 3-gallon container plant from a 6-cm division, about 120 days are usually required. Actual crop time will depend on temperature and time of division.

*Mature plant height.*—About 193 cm.

*Rhizomes.*—Robust and slightly creeping.

*Foliage description.*—Arrangement: Opposite, erect, sheathed. Shape: Linear. Margin: Entire. Aspect: Flat. Length: About 31 cm. Width: About 4.2 cm. Texture: Upper and lower surfaces smooth and glaucous. Color: Base color of 191A/191B with white overlaying bloom giving a grayed blue-green color, close to 190B. Fall and winter color varies from rust brown to warm tan depending on soil fertility levels. Culms: Clumping, sturdy, glaucous blue to purple.

Flower description:

*Inflorescence.*—Panicles very large, strong and open; panicles held mostly above the foliage; fine in texture. Rachis persistent throughout winter and spring. Flowering recurrent. Panicle branches spreading, feathery to slightly drooping.

*Natural flowering season.*—Late flowering compared to other cultivars of *Panicum virgatum*. Flowering from early September to first frost in the Northern Hemisphere.

*Quantity of inflorescences.*—Abundant from September until May.

*Panicle length.*—About 71 cm.

*Panicle diameter.*—About 31 cm.

*Panicle color.*—Glaucous blue to purple.

*Fragrance.*—None detectable.

*Glume size.*—Upper glume slightly shorter than spikelet, lower glume slightly shorter than upper glume.

*Spikelet length.*—About 8 mm.

*Spikelet shape.*—Elliptic/ovate.

Disease resistance: Resistance to fungal, bacterial or viral pathogens common to Panicum has not been observed.

Seed production: Seed production has been irregular, however germination of seed has not been observed.

It is claimed:

1. A new and distinct cultivar of Panicum plant named 'Dallas Blues', as illustrated and described.

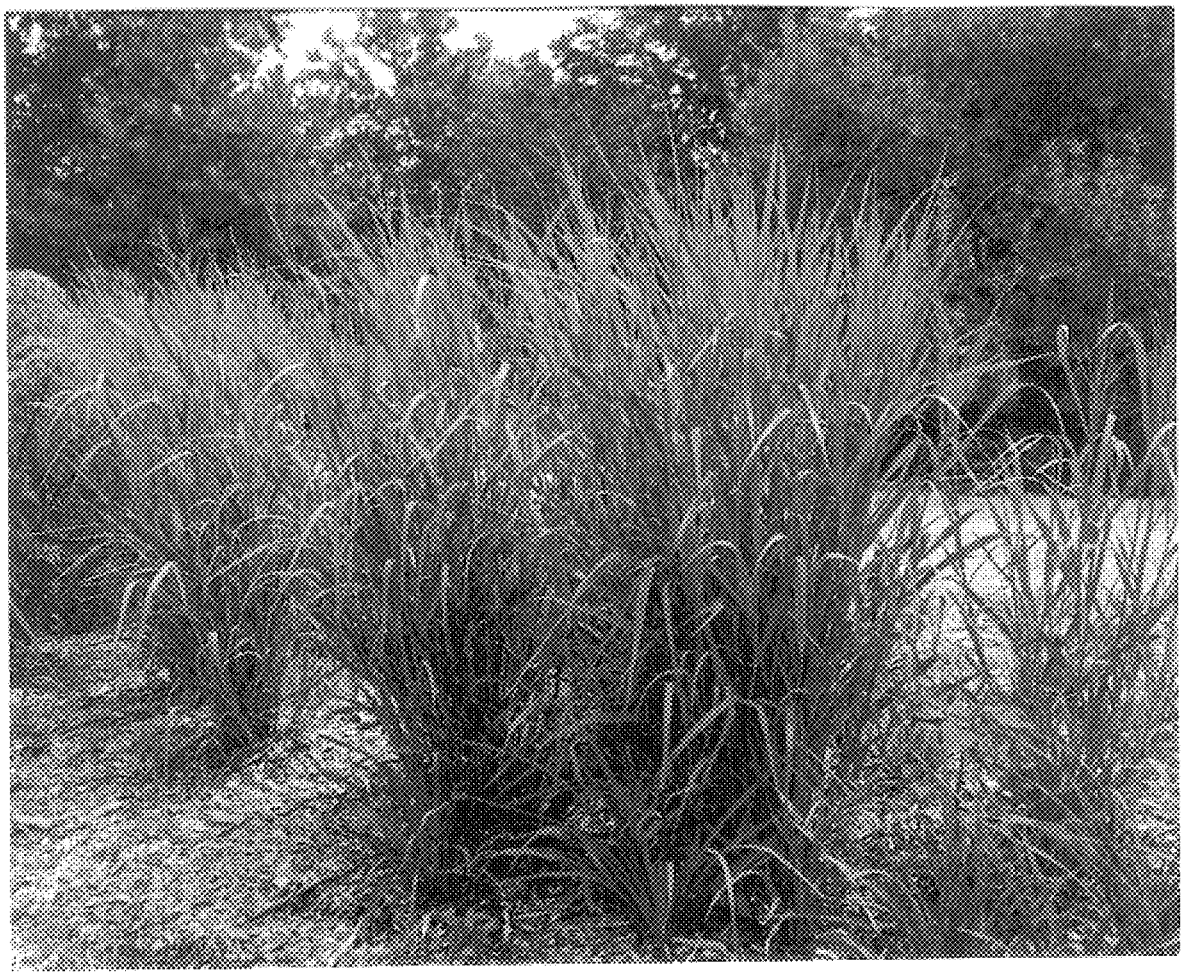

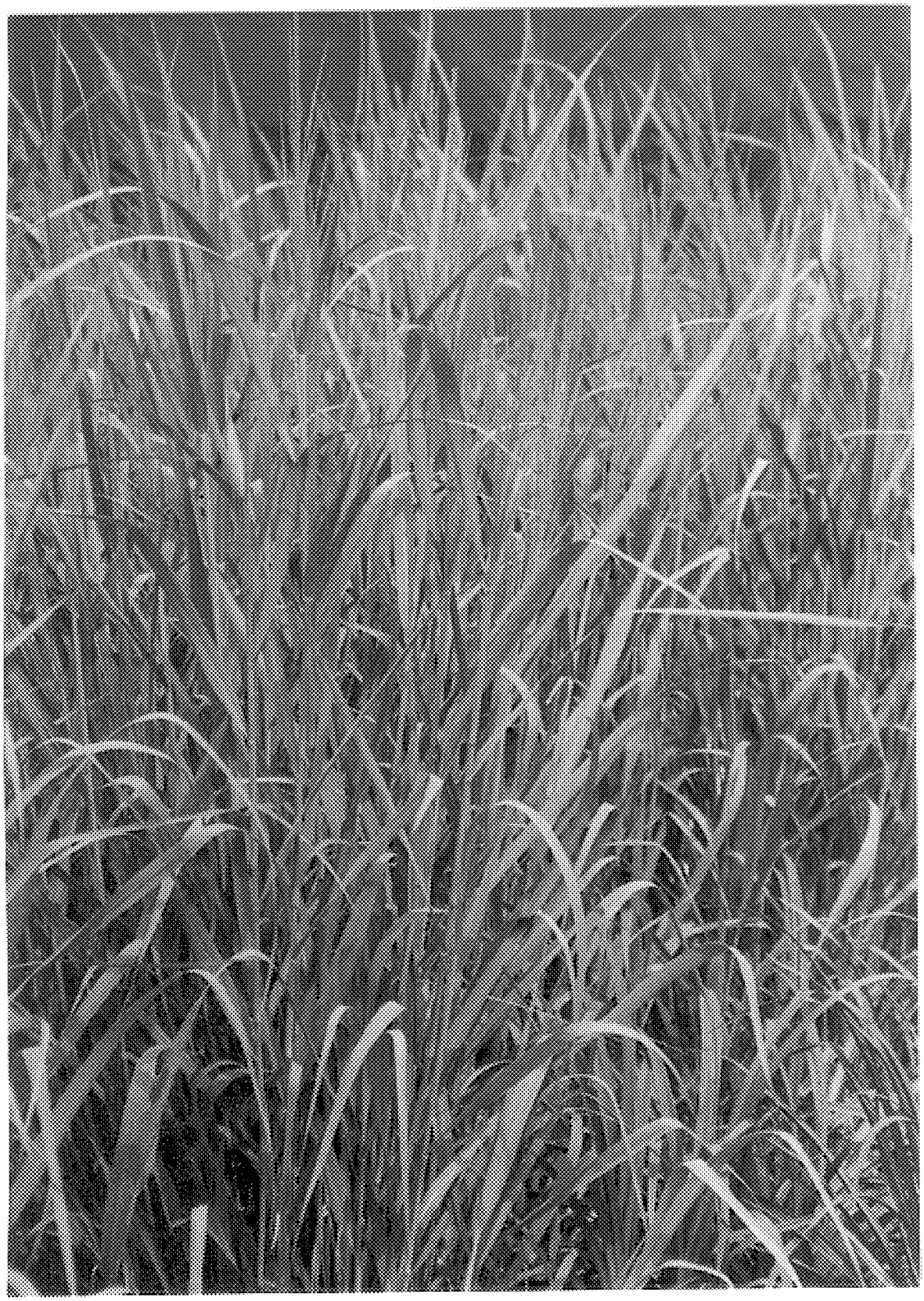

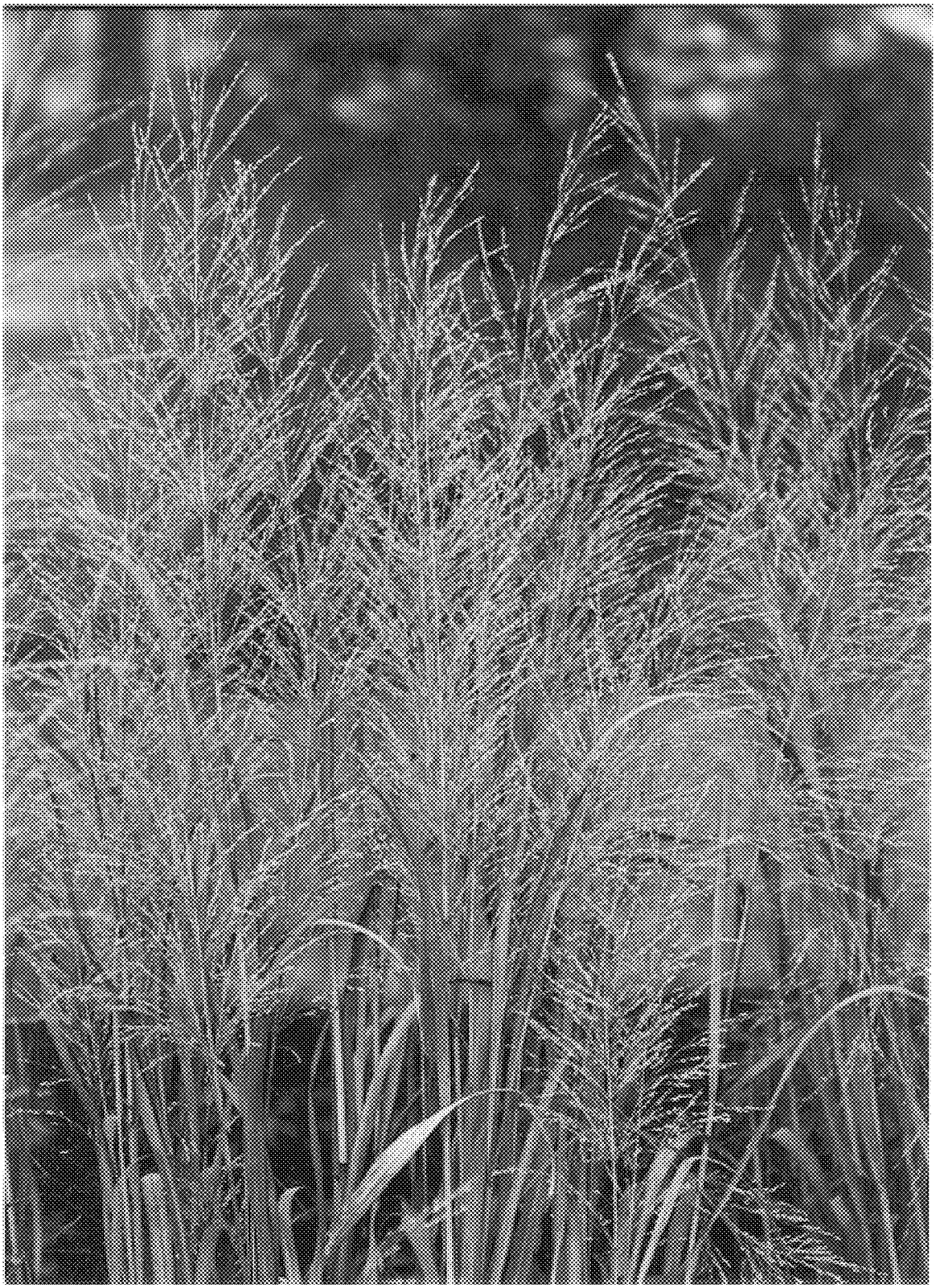

* * * * *